(12) United States Patent
Chu et al.

(10) Patent No.: US 6,720,431 B2
(45) Date of Patent: Apr. 13, 2004

(54) METHODS AND APPARATUS FOR SEPARATING AND DETECTING SPECIFIC POLYHALOGENATED DIAROMATIC HYDROCARBONS

(75) Inventors: Michael D. Chu, Durham, NC (US); George C. Clark, Durham, NC (US)

(73) Assignee: Xenobiotic Detection Systems International, Inc., Durham, NC (US)

( * ) Notice: Subject to any disclaimer, the term of this patent is extended or adjusted under 35 U.S.C. 154(b) by 0 days.

(21) Appl. No.: 09/872,758

(22) Filed: Jun. 1, 2001

(65) Prior Publication Data

US 2002/0035303 A1 Mar. 21, 2002

Related U.S. Application Data

(60) Provisional application No. 60/208,898, filed on Jun. 2, 2000.

(51) Int. Cl.⁷ .................. C07D 319/24; C07D 307/91; C07C 17/38

(52) U.S. Cl. .................. 549/359; 549/460; 570/211

(58) Field of Search ................. 549/359, 460; 570/211

(56) References Cited

U.S. PATENT DOCUMENTS

| | | | | |
|---|---|---|---|---|
| 4,110,344 A | * | 8/1978 | Stalling et al. | 549/359 |
| 5,071,820 A | * | 12/1991 | Quinn et al. | 502/434 |
| 5,854,010 A | | 12/1998 | Denison et al. | |

FOREIGN PATENT DOCUMENTS

| | | | | |
|---|---|---|---|---|
| JP | 60029341 | | 9/1985 | C01B/31/08 |

OTHER PUBLICATIONS

Feltz et al., Environmental Science and Technology, vol. 29(3), (1995) pp. 709–718.*
Smith, L.M. "Carbon Dispersed in Glass Fibers as an Adsorbent for Contaminant Enrichment and Fractionation." *Anal. Chem.* 53 (1981): 2152–2154.
Aarts, et al. "Application of the Chemical–Activated Luciferase Expression (CALUX) Bioassay for Quantifcation of Dioxin–Like Compounds in Small Samples of Human Milk and Blood Plasma". *Organohalogen Compounds* 27:285–290 (1996).
Ahlborg, et al. "Impact of Polychlorinated Dibenzo–p–dioxins, Dibenzofurans, and Biphenyls on Human and Environmental Health, with Special Emphasis on Application of the Toxic Equivalency Factor Concept." *European Journal of Pharmacology.* 228:179–199 (1992).
Ahlborg, et al. "Toxic Equivalency Factors for Dioxin–Like CBs" *Chemosphere* 28(6):1049–1067 (1994).
Bimbaum. "The Mechanism of Dioxin Toxicity: Relationship to Risk Assessment" *Environmental Health Perspectives* 102(Supplement 9): 157–167 (1994).

Creaser, et al. "Fractionation of Polychlorinated Biphenyls, Polychlorinated Dibenzo–p–Dioxins, and Polychlorinated Dibenzofurans on Porous Graphitic Carbon". *Anal. Chem.* 61:1300–1302 (1989).
Denison, et al. "The Ah Receptor: A Regulator of the Biochemical and Toxicological Actions of Structurally Diverse Chemicals" *Bull Environ Contam. Toxicol.* 61:557–568 (1998).
De Vito et al. Chapter 4: Toxicology of Dioxins and Related Chemicals *Dioxins and Health* Edited: Arnold Schecter. Plenum Press, New York pp. 139–162 (1994).
Elferink "The Ah Receptor Signal Transduction Pathway" *Toxicant–Receptor Interactions* Edited:Denison et al. Taylor & Francis, Philadelphia pp. 3–33. (1998).
Garrison, et al. "Species–Specific Recombinant Cell Lines as Bioassay Systems for the Detection of 2,3,7, 8–Tetrachlorodibenzo–p–Dioxin–Like Chemicals". *Fundamental and Applied Toxicology* 30:194–203 (1996).
Giesy, et al. Chapter 9: Dioxins Dibensofurans, PCBs and Colonial, Fish–Eating Water Birds *Dioxins and Health* Edited: Arnold Schecter. Plenum Press, New York pp. 249–307 (1994).
Giesy, et al. "Deformities in Birds of The Treat Lakes Region: Assigning Causality" *Environ. Sci. Technol.* 28(3):128A–135A (1994).
International Search Report corresponding to PCT/US01/17857. Mailed on Apr. 16, 2003.
Kocan, et al. "Method for the Group Separation of Non-Ortho–, Mono–Ortho–and Multi–Ortho–Substituted Polychlorinated Biphenyls and Polychlorinated Dibenzo–p–Dioxins/Polychlorinated Dibenzofurans Using Activated Carbon Chromatography". *Journal of Chromatography* 665:139–153 (1994).
Lafyatis, et al. "Poly(Furfuryl alcohol)–Derived Carbon Molecular Sieves: Dependence of Adsorptive Properties on Carbonization Temperature, Time, and Poly(ethylene glycol) Additives" *Ind. Eng. Chem. Res.* 30:865–873 (1991).
O'Keefe, et al. "Separation of Extracts from Biological Tissues into Polycyclic Aromatic Hydrocarbon, Polychlorinated Biphenyl and Polychlorinated Dibenzo–p–Dioxin/Polychlorinated Dibenzofuran Fractions Prior to Analysis" *Journal of Chromatography A* 771:169–179 (1997).

(List continued on next page.)

*Primary Examiner*—D. Margaret Seaman
(74) *Attorney, Agent, or Firm*—Myers Bigel Sibley & Sajovec, PA

(57) ABSTRACT

Sample processing methods that utilize a graphitised carbon matrix are useful for determining the relative amounts polyhalogenated biphenyls (PHBs), polyhalogenated dibenzofurans (PHDFs), and polyhalogenated dibenzo-p-dioxins (PHDDs) in a mixture of polyhalogenated diaromatic hydrocarbons (PHDHs). The methods are particularly useful when used in conjunction with cell-based assays for determining the toxicity of PHDH compounds.

85 Claims, 11 Drawing Sheets

OTHER PUBLICATIONS

Poland et al. "2,3,7,8–Tetracholorodibenzo–ρ–Dioxin and Related Halogenated Aromatic Hydrocarbons: Examination of the Mechanism of Toxicity" *Annual Review of Pharmacology and Toxicology: Vol. 22* Editors: George et al. pp. 517–542 (1982).

Ramos, et al. "Elution Pattern of Planar Chlorinated Biphenyls and 2,3,7,8–Polychlorinated Dibenzo–ρ–Dioxins/Dibenzofurnas on Chromatographic Adsorbents and Factors Affecting the Mechanism of Retention." *Journal of Chromatography A* 759:127–137 (1997).

Safe. "Polychlorinated Biphenyls (PCBs), Dibenzo–ρ–Dioxins (PCDDs), Dibenzofurans (PCDFs), and Related Compounds: Environmental and Mechanistic Considerations Which Support the Development of Toxic Equivalency Factors (TEFs)" *Toxicology* 21(1):51–88 (1990).

Safe. "Polychlorinated Biphenyls (PCBs): Environmental Impact, Biochemical and Toxic Responses, and Implications for Risk Assessment" *Critical Reviews in Toxicology* 24(2):87–149 (1994).

Safe. "Toxicology, Structure–Function Relationship, and Human and ?environmental Healtyh Impacts of Polychlorinated Biphenyls: Progress and Problems," *Envion Health Prospect* 100:259–268 (1993).

Safe. "Limitations of the Toxic Equivalency Factor Approach for Risk Assessment of TCDD and Related Compounds"*Teratogenesis, Carcinogenesis, and Mutagenesis* 17:285–304 (1997/98).

Sundstrom, et al. "In Vitro Bioassays for Toxic Polychlorinated Azobenzenes"*Chemosphere* 15(9–12):2105–2107 (1986).

Tanabe, et al. "Highly Toxic Coplanar PCBs: Occurrence, Source, Persistency and Toxic Implications to Wildlife and Humans" *Environmental Pollution.* 47:147–163 (1987).

Van den Berg, et al. "Human Risk Assessment and TEFs" *Food Additives and Contaminants* 17(4):347–358 (2000).

Van den Berg, et al. "Toxic Equivalency Factors (TEFs) for PCBs, PCDDs, PCDFs for Humans and Wildlife" *Environmental Health Perspectives* 106(12) 775–792 (1998).

United States Environmental Protection Agency (EPA) method 1613 (40 C.F.R. Part 1136) pp. 308–396.

United States Environmental Protection Agency (EPA) method 8290(40 C.F.R. Part 261).

Webster et al. Chapter 1: Overview; The Dioxin Debate. *Dioxins and Health* Edited: Arnold Schecter. Plenum Press, New York pp. 1–6 (1994).

\* cited by examiner

2 - 10 GRAM SAMPLE
TOLUENE, ACETONE HEXANE, OR METHANOL
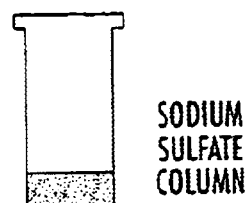
SODIUM SULFATE COLUMN
CONCENTRATE SAMPLE TO 1-2 ml HEXANE → DETERMINATION OF TOTAL PAHs AND PCDHs
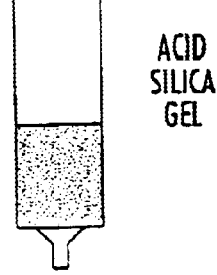
ACID SILICA GEL
→ CRUDE DETERMINATION OF PCDHs
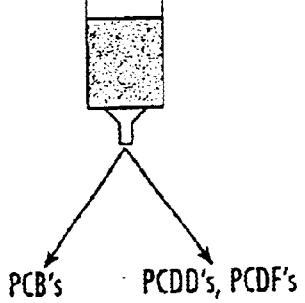
XCARB
PCB's    PCDD's, PCDF's → QUANTITATIVE DETERMINATION OF PCB's AND PCDDs/PCDFs
*FIG. 1.*

METHODS AND APPARATUS FOR SEPARATING AND DETECTING SPECIFIC POLYHALOGENATED DIAROMATIC HYDROCARBONS

RELATED APPLICATIONS

This application claims the benefit of U.S. Provisional Application No. 60/208,898, filed Jun. 2, 2000, which application is incorporated herein by reference in its entirety.

STATEMENT OF FEDERAL SUPPORT

This invention was made with government support under grant number ES08372-03 from the National Institutes of Health (Small Business Initiated Research). The United States government has certain rights to this invention.

FIELD OF THE INVENTION

This invention relates, in general, to analytical systems for separating and detecting polyhalogenated diaromatic hydrocarbons.

BACKGROUND OF THE INVENTION

Polyhalogenated diaromatic hydrocarbons (PHDHs) are a diverse group of widespread environmental contaminants that include polychlorinated biphenyls (PCBs), polychlorinated dibenzofurans (PCDFs), polychlorinated dibenzo-p-dioxins (PCDDs), polybrominated biphenyls (PBBs), polybrominated dibenzofurans (PBDFs), polybrominated dibenzo-p-dioxins (PBDDs), and other subclasses of PHDHs. See, e.g., Giesy et al, Chapter 9, pp. 249–307, *Dioxins and Health* (ed., A. Schechter, Plenum Press, New York, 1994). Of the PHDHs, the chlorinated compounds or polychlorinated diaromatic hydrocarbons (PCDHs) have been most widely studied. However, the environmental and health impacts of other PHDH compounds, such as polybrominated diaromatic hydrocarbons and mixed brominated/chlorinated diaromatic hydrocarbons are increasingly being recognized.

Many PHDHs are lipophilic and resistant to degradation, and have been detected in soil, sediment, and water. Moreover, many PHDHs have been found to concentrate and accordingly amplify their effect in the food chain. See, e.g., Giesy et al. (1994a), supra; Tanabe et al., *Environmental Pollution* 47, 147–163 (1987); Giesy et al, *Environmental Science and Technology*, 28, 128A–135A (1994b); Webster et al., Chapter 1, pp. 1–6, *Dioxins and Health* (ed., A. Schechter, Plenum Press, New York, 1994). Exposure to and bioaccumulation of PHDHs have been observed to produce a variety of deleterious species- and tissue-specific effects, including tumor promotion, birth defects, hepatotoxicity, immunotoxicity, dermal toxicity, alterations in endocrine homeostasis, undesirable induction of numerous enzymes (including cytochrome P450 1A1), and death. See e.g., Giesy et al., 1994b, supra, Poland et al., *Ann. Rev. Pharmacol. Toxicol.* 22, 517–542 (1982); Safe, *Critical Reviews in Toxicology* 24, 87–149 (1994); DeVito & Birnbaum, in *Dioxins and Health*, pp. 139–162 (ed., A. Schechter, Plenum Press, New York, 1994)

Known techniques for detection and quantification of PHDHs generally involve costly and time-consuming traditional instrumental analysis methods, such as gas chromatography separation (GC) and mass spectrometry (MS). These methods generally involve extensive sample processing before quantification and analysis. See, e.g., United States Environmental Protection Agency (EPA) Method 1613 (40 C.F.R. Part 136) and EPO Method 8290 (40 C.F.R. Part 261). High resolution gas chromatography/high resolution mass spectrometry (HRGC/HRMS) processing generally requires an extraction of the sample to be analyzed, then treatment of the resulting extract with acid and base compounds, followed by sequential separations (usually by chromatography techniques) on silica gel columns impregnated with, e.g., sulfuric acid, neutral alumina, silica gel and activated carbon; This multiple-step processing of sample extracts usually yields an extract sufficiently free of interfering compounds to yield a congener-specific quantification of many, but not all, toxic PHDHs using HRGC/HRMS detection.

A significant disadvantage of the HRGC/HRMS technique is that, in general, only polychlorinated compounds (e.g., PCDHs) can be quantified by the method. For example, analytical techniques for detecting/quantifying polybrominated compounds and mixed brominated/chlorinated compounds are currently very costly and their standards not well-established. Unfortunately, it is now thought that polybrominated or mixed polybrominated/polychlorinated compounds are as toxic or even more toxic than corresponding chlorinated isomers. There accordingly remains a need for systems and methods that can determine and quantify toxic compounds not detectable by the HRGC/HRMS methods, such as toxic polybrominated or mixed polybrominated/polychlorinated diaromatic hydrocarbons.

Moreover, although HRGC/HRMS analysis allows detection and quantification of mixtures of known PCDH isomers and congeners, the method generally does not provide any information about the biological and/or toxicological effects of these complex mixtures. These mixtures, under certain environmental conditions, may theoretically contain up to or even more than 210 different PCBs, 135 different PCDFs, and 75 different PCDD isomers and congeners, each of which have vastly different chemical, physical, and toxicological properties. See Safe, 1994, supra, and Safe, *Critical Reviews in Toxicology* 21, 51–88 (1990).

Accordingly, accurate prediction of the biological/toxic activity of complex PCDH mixtures using HRGC/HRMS is difficult. Consequently, the toxicological potency of a complex mixture of PCDH chemicals is generally assessed by the toxic equivalent factor (TEF) approach, in which the concentration of individual compounds present in the PCDH mixture are multiplied by their specific TEF, and the sum of the values expressed as toxic equivalents (TEQs). See Safe, 1994, supra; Safe, 1990, supra; and Ahlborg et al., *European J. of Pharmacol and Environmental Toxicology* 228, 179–199 (1992).

It is generally thought that many effects of PHDDs, PHDFs, and dioxin-like PHBs proceed through the action of the aryl hydrocarbon receptor (AhR), a cytosolic protein that binds these compounds with high affinity (Safe 1990, supra; S. Safe, *Environ. Health Perspect.* 100, 259–268 (1992); Safe 1994, supra; L. S. Birnbaum, *Environ. Health Perspect.* 102, Suppl. 9, 157–167 (1994); M. S. Denison and S. Heath-Pagliuso, *Bulletin of Environmental Contamination and Toxicology* 61, 557–568 (1998); M. S. Denison et al., "The Ah receptor signal transduction pathway," in Denison, M. S., Helferich, (Eds.), *Xenobiotics, receptors and gene expression* (Taylor and Francis, Philadelphia, pp. 3–33, 1998a). The occurrence of this common mechanism supports the continued use of the TEF concept.

PCDDs and PCDFs with chlorine substitutions in the 2-,3-,7-, and 8-positions exhibit the highest affinity binding to the AhR and the strongest toxic effects, with increasing chlorination generally reducing potency. The toxic potencies of the different congeners relative to 2,3,7,8-tetrachlorodibenzo-p-dioxin (2,3,7,8-TCDD), the most toxic dioxin, are indicated by their corresponding toxic equivalency factors (TEFs). Over the past decade, a number of different TEF schemes have been proposed. See e.g., U. G. Ahlborg, *Chemosphere* 28, 1049–1067 (1994); M. Van den Berg et al., *Environ. Health Perspect.* 103, 775–792 (1998); S. Safe, *Teratogenesis, Carcinogenesis and Mutagenesis* 17, 285–304 (1997–98). The most recent consensus TEFs for humans, fish and wildlife risk assessment were derived at a WHO/IPCS (World Health Organization/International Programme on Chemical Safety) meeting held in Stockholm, Sweden on Jun. 15–18, 1997. See Van den Berg et al., 1998, supra, and M. Van den Berg, *Food Add. Contam.* 17, 347–358 (2000). TEFs have been assigned to seven PCDDs, ten PCDFs and twelve PCBs, and range from 0.00001 to 1, reflecting a pronounced variability in toxicity.

Hazard and risk assessments of chemicals carried out by regulatory agencies have primarily addressed the toxicities of individual compounds, whereas humans and wildlife are exposed to complex mixtures of toxic compounds (Safe, 1998, supra). In addition to PCDDs, PCDFs, and dioxin-like PCBs, a number of other compounds exert AhR-agonist activity. In 1998, the international WHO committee agreed that other halogenated chemicals meet the criteria for inclusion in the TEF concept, but maintained that insufficient environmental and toxicological data were available to establish TEF values for these compounds (Van den Berg et al., 1998, supra). A few examples of these compounds, detailed further below, are brominated and mixed chloro/bromo-substituted analogues of PCDDs, PCDFs and PCBs, halogenated naphthalenes, halogenated diphenyl ethers, halogenated azo- and azoxybenzenes and polycyclic aromatic hydrocarbons (PAHs). See, e.g., G. Sundstrom et al., *Chemosphere* 15, 2105–2107 1986; Birnbaum, 1994, supra; Denison and Heath-Pagliuso, 1998, supra; and Denison et al., 1998b, supra.

Cell-based bioassays have been combined with extraction technology and acid silica gel column chromatography in order to improve the analysis of the specificity of PCDHs contaminating environmental samples. For example, in one known methodology, the correlation of the determination of specific content of PCDHs with the results of traditional HRGS/HRMS techniques was about 0.71. However, this methodology and others have certain disadvantages, including the inability to quantify the content of PCBs relative to the content of the dioxin/furan class of PCDHs in a mixture. See J. M. Aarts et al., *Organohalogen Compounds* 27, 285–289 (1996).

Cell bioassay systems have been developed to directly quantify TEQ activity based upon a concentration-specific expression of the toxicity of certain PCDHs. U.S. Pat. No. 5,854,010 to Denison et al. (hereinafter the "+010" patent, which patent is incorporated by reference herein in its entirety) describes a detection system based on a novel recombinant cell line that responds to certain polyaromatic hydrocarbons by expressing the reporter compound luciferase. See also P. M. Garrison, et al., *Fundam. Appl. Toxicol.* 30, 194–203 (1996). In other words, the bioassay system of the '010 patent (also and hereinafter interchangeably referred to as the CALUX® system) responds to the presence of certain polyaromatic hydrocarbons by luminescence, which can be quantified and ultimately accurately correlated with the amount of the polyaromatic hydrocarbons present in a sample.

Despite having advantages over previous methods of polyaromatic hydrocarbon quantification, the system described by the '010 patent still requires time-consuming sample processing methods in order to provide results that reliably correlate with the results obtained with isomer-specific detection by HRGC/HRMS methods generally used for regulatory purposes (i.e., EPA Methods 8290 and 1613). Accordingly, a need still exists for reliable and convenient sample processing techniques for separating individual types of PHDH compounds (e.g., PCDH and PBDH compounds) for quantification and analysis. Additionally, sample processing and evaluation techniques are needed for determining the presence and toxicity of a broad range of toxic polyhalogenated compounds, including polybrominated and mixed brominated/chlorinated compounds.

SUMMARY OF THE INVENTION

The present inventors have discovered a rapid, relatively inexpensive methodology to quantify TEQ contributed by polyhalogenated biphenyls (e.g., PCBs and PBBs), and/or dioxins and/or furans of the PHDH class of compounds. In one embodiment, the current invention describes separation methods useful for providing samples for the isolation and specific detection of 2,3,7,8-tetrachlorodibeno-para-dioxin and related toxic congeners from the family of polychlorinated diaromatic hydrocarbons (PCDH). The method allows for the quantification of specific toxic compounds of the PHDH family of compounds. The inventive method also allows for accurate resolution of the toxicity due to polyhalogenated, and particularly, polychlorinated dibenzodioxins and furans respective to the toxicity contributed by the polyhalogenated, and particularly polychlorinated biphenyls.

Accordingly, the present invention provides sample processing methods for the quantitative analysis of certain polyaromatic hydrocarbons (and particularly, polyhalogenated diaromatic hydrocarbons). One embodiment of the method comprises separating components of a polyaromatic hydrocarbon mixture from a sample and determining the amount of both total polyaromatic hydrocarbons and specific families of polyaromatic hydrocarbons in the sample.

In certain embodiments, the present method may be used in conjunction with known methods for quantifying families of polyaromatic hydrocarbon compounds within complex mixtures. Such quantifying methods include but are not limited recombinant bioassay systems for testing for polyhalogenated diaromatic hydrocarbons, and, in the case of polychlorinated diaromatic hydrocarbons, traditional chemical analysis of gas chromatography with electron capture detection (GC/ECD) and analysis with high resolution gas chromatography high resolution mass spectrometry (HRGC/HRMS).

In a preferred embodiment, the quantification method is the bioassay system known as the CALUX® system described in U.S. Pat. No. 5,854,010 (incorporated by reference herein in its entirety), which utilizes using a recombinant cell line deposited at the American Type Culture Collection under accession number CRL-12286 (also known and referred to herein interchangeably as the "mouse H1L1.1 cell line").

The present invention method advantageously allows for the preparation of a sample so that multiple determinations can be made of the content of the polyaromatic hydrocarbons present in the sample. Certain embodiments of the invention allow for individual quantification of all polyaromatic hydrocarbons that are present in the sample. Additional aspects of the invention provide for the removal of certain chemical substances that are not of the class of compounds that are PHDHs.

Using the inventive methods described herein, PHDHs, and particularly, PCDHs can be quantified by adsorption to an affinity matrix as described herein. These methods may optionally measure/quantify the amount of compounds in a sample that belong to the group of compounds known as planar polychlorinated biphenyls (PCBs), as well as the amount of compounds in a sample that belong to the group comprising polychlorinated dibenzo-para-dioxins (PCDDs) and polychlorinated dibenzofurans (PCDFs). These methods may optionally measure/quantify the amount of compounds in a sample that belong to the group of compounds known as planar polybrominated biphenyls (PBBs), as well as the amount of compounds in the sample that belong to the group comprising polybrominated dibenzo-para-dioxins (PBDDs) and polybrominated dibenzofurans (PBDFs). In even other alternative embodiments, these methods may measure/quantify the amount of compounds in a sample that belong to the groups of compounds that are planar mixed polybrominated/polychlorinated biphenyls, as well as the amount of compounds in the sample that belong to the groups comprising mixed polybrominated/polychlorinated dibenzo-para-dioxins and mixed polybrominated/polychlorinated dibenzofurans.

The foregoing and other aspects of the present invention are explained in detail in the specification set forth below.

BRIEF DESCRIPTION OF THE DRAWINGS

FIG. 1 is a schematic showing the overall procedure for processing samples for the determination of total polyaromatic hydrocarbons/PCDHs contained in a sample, and separation procedures for determining individual amounts of total PCDHs, PCBs, and dioxins and furans in a sample.

DETAILED DESCRIPTION OF THE INVENTION

Figure 2:
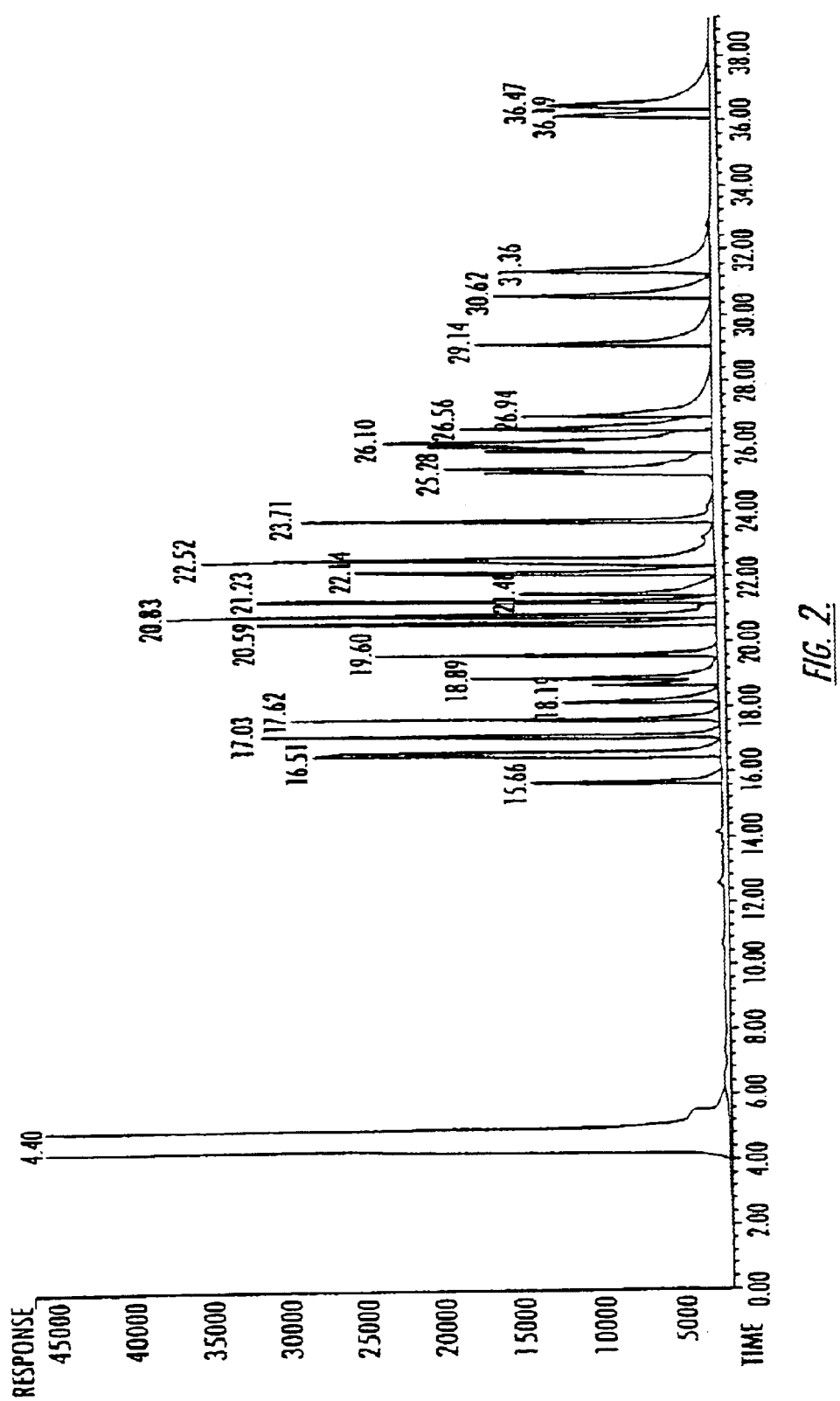
FIG. 2 is a chromatograph of one test mixture of polychlorinated biphenyls and polychlorinated dibenzodioxins/furans as measured by gas chromatography and electron capture detection.

The present invention will now be described more fully hereinafter with reference to the accompanying drawings and specification, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only, and is not intended to be limiting of the invention. As used in the description of the invention and the appended claims, the singular forms "a", "an" and "the" are intended to include the plural forms as well, unless the context clearly indicates otherwise. All publications, patent applications, patents, and other references mentioned herein are incorporated by reference in their entirety.

Abbreviations and Acronyms

The following abbreviations and acronyms are employed for convenience and clarity throughout this specification.

| ABBREVIATION | DEFINITION |
| --- | --- |
| PAH | polyaromatic hydrocarbon |
| BA | benz[a]anthracene, a PAH |
| BNF | β-naphthoflavone, a PAH |
| 3-MC | 3-methylcholanthrene, a PAH |
| PHDH | polyhalogenated di-aromatic hydrocarbon, a PAH |
| PCDH | polychlorinated di-aromatic hydrocarbon, a PAH |
| PBB | polybrominated biphenyl, a PHDH |
| PCB | polychlorinated biphenyl, a PCDH |
| AROCLOR ® 1242 | trade name of a mixture of PCBs with an average 42% chlorination |
| AROCLOR ® 1254 | trade name of a mixture of PCBs with an average 54% chlorination |
| AROCLOR ® 1260 | trade name of a mixture of PCBs with an average 60% chlorination |
| 3,3',4,4'-TCB | 3,3',4,4'-tetrachlorobiphenyl, a kind of PCB |
| 3,3',4,4',5-PCB | 3,3',4,4',5-pentachlorobiphenyl, a kind of PCB |
| 2,3,4,4',5-PCB | 2,3,4,4',5-pentachlorobiphenyl, a kind of PCB |
| 2,3,3',4,4',5-HCB | 2,3,3',4,4',5-hexachlorobiphenyl, a kind of PCB |
| 2,2',5,5'-TCB | 2,2',5,5'-tetrachlorobiphenyl, a kind of PCB |
| PHDF | polyhalogenated dibenzofuran, a kind of PHDH |
| PCDF | polychlorinated dibenzofuran, a kind of PCDH |
| PBDF | polybrominated dibenzofuran, a kind of PCDH |
| 2,3,7,8-TCDF | 2,3,7,8-tetrachlorodibenzofuran, a kind of PCDF |
| 2,3,4,7,8-PCDF | 2,3,4,7,8-pentachlorodibenzofuran, a kind of PCDF |
| PCDD | polychlorinated dibenzo-p-dioxin, a kind of PCDH |
| PBDD | polybrominated dibenzo-p-dioxin, a kind of PCDH |

-continued

| ABBREVIATION | DEFINITION |
|---|---|
| PHDD | polyhalogenated dibenzo-p-dioxin, a kind of PHDH |
| TCDD | 2,3,7,8-tetrachlorodibenzo-p-dioxin, a kind of PCDD |
| 1,2,4,7,8-PCDD | 1,2,4,7,8-pentachlorodibenzo-p-dioxin, a kind of PCDD |
| EROD | 7-ethoxyresorufin-O-deethylase enzyme |
| AHH | aryl hydrocarbon hydroxylase enzyme |
| PM | pico molar, $1 \times 10^{-12}$ molar |
| NM | nano molar, $1 \times 10^{-9}$ molar |
| PAP or pap | placental alkaline phosphatase enzyme |
| DMSO | dimethyl sulfoxide |
| MDL | minimal detection level |
| RLU | relative light unit |
| PBS | phosphate buffered saline |
| G418 ® | trade name of an antibiotic from Gibco |
| $ED_{50}$ | toxic equivalent factors for PCDHs measured by their ability to induce EROD/AHH activity in cell cultures |
| TCDD-like PAHs | compounds that are not dioxins, but that will cause the novel mouse H1L1.1 cell line (described herein) to respond with luminescence in the way TCDD causes the novel mouse H1L1.1 cell line to respond with luminescence; examples include TCDD-like fused-ring polyaromatic hydrocarbon compounds, TCDD-like polychlorinated di-aromatic hydrocarbon compounds, and combinations thereof |
| TEF | toxic equivalent factor |
| TEQ | toxic equivalents |
| CALUX | Chemical Activated Luciferase gene eXpression |

The present invention encompasses the preparation of an inventive absorption matrix that absorbs PHDHs (e.g., PCDHs, PBDHs) and specifically absorbs PCBs, dioxins and furans from environmental samples.

As used herein, the terms "samples" and "environmental samples" include solid, liquid and gaseous samples, both naturally-occurring and non-naturally occurring. By way of example only, samples that may be analyzed by the present invention include sediment, soil, and ash samples, water samples (i.e., groundwater samples, drinking water samples, wastewater or effluent samples), other liquid samples, solid and liquid food samples (or extracts of the same), including milk, meat, fruit, packaged or unpackaged food, and pre-served or non-preserved foods. Gaseous samples include, but are not limited to, automotive or industrial exhaust gas. The term "sample" also encompasses biological samples from a human, a non-human animal, or a plant subject, including bodily fluid, blood, tissue, fat, biopsy, cell, leaf, root, and seed samples.

Polyhalogenated diaromatic hydrocarbons detectable in the methods of the present invention include, but are not limited to, toxic compounds such as 2,3,7,8-tetrachlorodibenzodioxin, 2,3,7,8-tetrachlorodibenzofuran, and their isomers, as well as the coplanar polychlorinated biphenyls (PCBs) and polybrominated biphenyls (PBBs) that cause toxicity through a similar mechanism of action. Preferably, the polyaromatic hydrocarbons that may be detected by the present invention include polychlorinated dibenzo-para-dioxins (such as 2,3,7,8-tetrachlorodibenzo-para-dioxin) and TCDD-like compounds (such as TCDD-like fused-ring polyaromatic hydrocarbon compounds and TCDD-like polychlorinated di-aromatic hydrocarbon compounds). Also, and preferably, the TCDD-like polychlorinated di-aromatic hydrocarbon compounds that may be detected by the present invention include compounds such as polychlorinated dibenzofurans and coplanar polychlorinated biphenyls, and polybrominated dibenzofurans and coplanar polybrominated biphenyls.

FIG. 1 illustrates one embodiment of the invention, and is an overall schematic of a method for extracting and treating samples according to the present invention. One aspect of the method is the extraction of the polychlorinated diaromatic hydrocarbons (PCDHs) (e.g., PCBs, dioxins and furans) contained in a sample to yield a "first extracted sample." Extraction of the PCDH compounds in the sample facilitates the concentration and processing of the particular compounds contained in the sample. The extraction of PCDH compounds preferably utilizes a chromatography matrix or column that facilitates the removal of particulate substances that could potentially interfere with processing and quantification of the PCDH compounds contained in the extract. The first extracted sample will thus preferably comprise the total amount of PCDH compounds in the sample. If so desired, the skilled artisan may make a quantitative or qualitative measurement of the total PCDH compounds in the sample, using methods known in the art.

The extraction of PCDH compounds to produce a first extracted sample may be accomplished by sonication of samples with a mixture of organic solvents that allow partitioning into an organic phase. In a preferred embodiment, the solvent mixture is a mixture of methanol and toluene, and more preferably a mixture of methanol and toluene in which methanol comprises about 15–25%, and preferably about 20% of the mixture, while toluene comprises about 60–90%, and preferably about 80% of the mixture. The organic phase is separated, preferably by chromatography, in order to remove residual aqueous components (e.g., water). In a preferred embodiment, the organic phase is separated over a sodium sulfate column to remove any residual aqueous phase. After separation, the organic phase is concentrated, preferably by vacuum centrifugation.

As illustrated in FIG. 1, an optional purification step may be carried out on the first extracted sample in order to remove contaminants such as polyaromatic hydrocarbons that are not as toxic as the PCBs, dioxins and furans that are desirably detected by the present method (i.e., those polyaromatic hydrocarbons that need not be detected or quantified, and/or are not subject to governmental regulation because of persistence and toxicity). The optional purification step is preferably carried out by using a second chromatography matrix or column to yield a "purified first extracted sample." In one embodiment, the first extracted sample is separated with a silica gel column treated with about 30% sulfuric acid (i.e., an acid-silica column) and eluted with an organic solvent such as hexane, in order to produce the purified first extracted sample.

The first extracted sample (optionally and preferably, a purified first extracted sample eluted from an acid-silica column) is then applied to another chromatography matrix or column comprising activated carbon and diatomaceous earth (referred to herein as an "XCARB column"). This processing step, also illustrated in FIG. 1, utilizes an activated carbon affinity matrix that provides unique specificity and the ability to allow individual quantification of PCBs respective to (i.e., versus or in comparison to) the amount of dioxins and furans of the PCDH class of compounds that are present in the sample.

Many types of diatomaceous earth are known in the art and are commercially available, but in a preferred embodiment, the diatomaceous earth is the commercially available Celite®, which can be purchased from Sigma (St. Louis, Mo.).

The activated carbon of the XCARB column is preferably graphitized carbon. In a preferred embodiment, the activated carbon is a carbon molecular sieve. Carbon molecular sieves suitable for use in preparing the metal-containing catalysts are well known in the art, and are generally amorphous materials with average pore dimensions similar to the critical dimensions of individual molecules. These carbon-based absorbents are also referred to as ultra-microporous carbons, and contain a relatively large specific pore volume, primarily in pores of molecular dimensions. These carbon forms are generally obtained by the controlled pyrolysis of natural and synthetic precursors, including coal, coconut shells, pitch, phenolformaldehyde resins, styrene-vinyl benzene sulfonated resins, polyfurfuryl alcohol, polyacrylonitrile, and polyvinylidene chloride. Suitable precursors may be cross-linked and may contain a cation, anion, strong base, weak base, sulfonic acid, carboxylic acid, halogen, or alkyl amine functionality. The chemistry of such materials is reviewed, for example, in Foley, "Carbon Molecular Sieves Properties and Applications in Perspective", in *Perspectives in Molecular Sieve Science,* Flank et al., (American Chemical Society, pp. 335–360 (1988)), Schmitt, "Carbon Molecular Sieves as Selective Catalyst Supports-10 Years Later," in *Carbon,* 29(6), 743–745 (1991), and Walker, "Carbon-An Old But New Material Revisited", in *Carbon,* 28 (2/3), 261–279 (1990). In preferred embodiments, the carbon used in the activated carbon column forms planar sheets on the molecular level, such that planar molecules are able to be absorbed onto the carbon via, for example, Van der Waals forces.

Certain carbon molecular sieves are available from commercial sources and may also be utilized in the present invention. Useful carbon molecular sieves include, for example, the Ambersorb series of absorbent offered by the Rohm and Haas Company (e.g., "Ambersorb 563", "Ambersorb 564", "Ambersorb 572", "Ambersorb 575", "Ambersorb 348F"), as well as the carbon molecular sieve materials available from Amoco ("PX-21 "), Anderson Development Company ("AX-21" and "Super AX-21"), Calgon Carbon Corporation ("Calgon MSC-V"), Alltech Associates ("Carbosphere"), Takeda ("5A Carbon"), and Tokai Carbon Co., Ltd., Tokyo, Japan ("TOKABLACK"). References describing methods of preparing carbon molecular sieves useful in the present invention include Lafyatis et al., *Ind. Eng. Chem. Res.* 30, 865–873 (1991), Japanese Kokai No. 61-191,510 (abstracted in *Chem. Abst.* 105: 229264y), U.S. Pat. No. 4,082,694 to Wennerberg et al., U.S. Pat. No. 4,839,331 to Maroldo et al., U.S. Pat. No. 4,040,990 to Neely, and U.S. Pat. No. 4,528,281 to Sutt, among others; the teachings of these publications are incorporated herein by reference in their entirety.

The graphitized and activated carbon is optionally and preferably heated prior to use in the column. The temperature at which and length of time that the carbon is heated will depend on the specific material used, but may be at about 100° C., or about 200° C., or about 250° C., or about 300° C., or about 400° C., or about 500° C., or about 600° C., or about 700° C., or about 800° C., or even higher, as can be determined by one skilled in the art. Preferably, the carbon is treated at about 200° C. or about 250° C. The activated carbon may be heated for one or more hours, or for one or more days (e.g., from about one to about fourteen days, or about twenty-one days, or about 30 days), or for one or more weeks (e.g., about one week, or about two weeks, or about three weeks, or about four weeks), or for one or months (e.g., one month, or two months, or three months) or even longer, as can be determined by one skilled in the art. In a preferred embodiment, the carbon is treated for about thirty days.

In one preferred embodiment, the activated carbon molecular sieve is activated carbon AX-21 from Anderson Chemical Company (Adrian, Mich.), and is treated prior to use by heating the activated carbon for about 30 days at about 200° C. In another preferred embodiment, the activated carbon molecular sieve is GRAFOIL® grade TG-407 flexible graphite powder from the UCAR Carbon Company (Cleveland, Ohio). In this embodiment, the particle size of the GRAFOIL® is preferably from about 20 to about 40 microns in particle size. As with the other carbon materials useful in the present invention, the GRAFOIL® may or may not be heated prior to use.

The XCARB column specifically retains PCDH compounds that are planar and possess TEQ activity. After contacting the sample with the column, the column is then preferably washed with an organic solvent (e.g., hexane). In one embodiment, the dioxin and furan PCDH compounds (e.g., PCDDs and PCDFs) are eluted from the column with a small volume of organic solvent such as toluene, in order to yield a "dioxin/furan fraction". PCB compounds may be eluted from the column by elution with another organic solvent, such as a solution of 25% toluene in hexane, or preferably with a solution of 10% toluene/10% ethyl acetate/ 80% hexane, to yield a "PCB fraction." The dioxin/furan fraction and/or the PCB fraction may optionally be dried for further analysis.

The PCB and dioxin/furan fraction eluted from the XCARB column may optionally be additionally purified, separated or concentrated by any one of several methods known in the art. For example, fractions eluted from the XCARB column may be further purified by utilizing alumina purification techniques that are set forth in, EPA Method 8290 [Analysis of PCDDs and PCDFs by High Resolution Gas Chromatography/High Resolution Mass Spectrometry (HRGC/HRMS)].

Fractions eluted from the XCARB column (which optionally have been further purified) may be concentrated to dryness and dissolved in an organic solvent such as hexane. In certain embodiments, an appropriate volume of of dimethyl sulfoxide (DMSO) is added to the test tube prior to the fraction being concentrated to dryness.

Dried fractions may then be quantified by one of several known methods for quantifying types of PHDH compounds within complex mixtures. Such quantifying methods include but are not limited recombinant bioassay systems for testing for polyhalogenated di-aromatic hydrocarbons, and, in the case of polychlorinated di-aromatic hydrocarbons, traditional chemical analysis of gas chromatography with electron capture detection (GC/ECD) and analysis with high resolution gas chromatography high resolution mass spectrometry (HRGC/HRMS).

In a preferred embodiment, the quantification method is the in vitro bioassay system known as the CALUX® system described in U.S. Pat. No. 5,854,010 (incorporated by reference herein in its entirety), which utilizes a recombinant cell line deposited at the American Type Culture Collection under accession number CRL-12286 (also known and referred to in interchangeably as the "mouse H1L1.1 cell line" or "mouse hepatoma H1L.1.1 cell line"). In preferred embodiments of this invention, the mouse H1L.1 cell line is stably transfected with a vector (e.g., the pGudLuc1.1 vector) that contains a gene (or coding region thereof) for the luminescent enzyme firefly luciferase, which in turn is under transactivational (transcriptional) control of the aryl hydrocarbon receptor (Ah receptor or AhR). The recombinant cell lines respond to exposure to polyhalogenated diaromatic hydrocarbons with the induction of luciferase, which in the presence of its substrate triggers a luminescence signal proportional to the cells' response. The measured luminescence is converted into a TEQ value by direct comparison of the response for a given sample to that obtained for a (as an example) 2,3,7,8-TCDD dose response curve (see, e.g., Garrison et al., 1996, supra; M. H. Ziccardi, *Toxicol. Sci.* 54, 183–193 (2000)). Advantageously, the CALUX® in vitro cell bioassay detects all compounds that can activate AhR and AhR-dependent gene expression (i.e., AhR agonists), including compounds not easily quantified by HRGC/HRMS, such as polybrominated compounds and mixed brominated/chlorinated compounds.

In summary, the present invention encompasses the preparation of a specific novel absorption matrix that is useful for absorbing PHDHs, and more particularly PCDHs, and even more particularly PCBs, dioxins and furans from environmental samples. Also described is methodology useful in preparing sample extracts with the novel absorption matrix to allow quantification of TEQ activity of PHDHs, and specifically PCDHs, and even more particularly PCBs, dioxins and furans from environmental samples.

The following Examples are provided to illustrate the present invention, and should not be construed as limiting thereof. In the following Examples, the mixtures of PCBs, dioxins and furans were purchased from Accustandard (New Haven, Conn.), and contain the following chemical compounds: A=2,3,7,8-TCDD, B=1,2,3,7,8-PeCDD, C=1,2,3,4, 7,8-HxCDD, D=1,2,3,6,7,8-HxCDD, E=1,2,3,7,8,9-HxCDD, F=1,2,3,4,6,7,8-HpCDD, G=1,2,3,4,6,7,8,9-OCDD, H=2,3,7,8-TCDF, I=1,2,3,7,8-PeCDF, J=2,3,4,7,8-PeCDF,K=1,2,3,4,7,8-HxCDF, L=1,2,3,6,7,8-HxCDF, M=1, 2,3,7,8,9-HxCDF, N=2,3,4,6,7,8-HxDCF, O=1,2,3,4,6,7,8-HpCDF, P=1,2,3,4,7,8,9-HpCDF, Q=1,2,3,4,6,7,8,9-OCDF. PCB standards included 1=3,3',3,4' Tetrachlorobiphenyl, 2=2,3,4,4',5 Pentachlorobiphenyl, 3=2,3',4,4',5 Pentachlorobiphenyl, 4=2,3,4,4',5 Pentachlorobiphenyl, 5=2,3,3',4,4' Pentachlorobiphenyl, 6=3,3',4,4'5 Penta chlorobiphenyl, 7=2,3',4,4',5,5' Hexa chlorobiphenyl, 8=2, 3,3',4,4',5 Hexa chlorobiphenyl, 9=2,3,3',4,4',5' Hexa chlorobiphenyl, 11=3,3',4,4',5,5' Hexa chlorobiphenyl, 13=2,3,3',4,4',5,5' Hepta chlorobiphenyl. Unknown samples and GC/MS data were supplied by the Hiyoshi-Corporation (Japan).

EXAMPLE 1

Preparation of XCARB Affinity Matrix Column for Isolation of PCDHs

An adsorption matrix is prepared by heating carbon AX-21 for thirty days at 200° C. in an oven. The resulting material specifically adsorbs PCDHs, including PCBs, polyhalogenated dioxins and furans. The treated AX-21 is mixed in the ratio 1:99 with Celite® to make a specific binding or affinity matrix referred to herein as "XCARB." An affinity column is prepared by placing and compacting a plug of glass wool into a glass column measuring sixteen inches long to a position seven inches from the end of the column. 0.3 cc of sodium sulfate is added to the column and the column is gently tapped. Then 0.7 cc of XCARB is added to the column and the column is gently tapped. Another 0.3 cc of sodium sulfate is added to the column and the carbon is gently tapped. Finally, a plug of glass wool that will retain the packing material in the column is gently pressed against the packing material. The XCARB column is then washed by sequentially washing with 5 ml of acetone, 20 ml of toluene, and 10 ml of hexane.

EXAMPLE 2

Preparation of Solid Samples for Quantification of TEQs of PCDHs

A mass of solid sample is weighed out into a glass vial. The mass of the sample will depend on the expected concentrations of contaminating PCDHs but is usually between one to five grams of sample. To the sample is added 10 ml of 20% methanol in toluene. The sample is sonicated in a water bath for five minutes.

A drying column is prepared to pass the sample extract through for collection purposes. The drying column consists of a 25 ml glass column to which a glass wool plug has been added to retain packing materials. The first packing material added to the drying column consists is 1 cc of Celite® followed by 4.3 cc of sodium sulfate. The drying column is washed with 30 ml of hexane before collection of sample extracts.

The first sample extract is passed through the drying column and collected into a 50 ml culture tube or other suitable collection vessel. To the sample is added an additional 10 ml of toluene and the sample is sonicated for 5 minutes in a water bath. The second extraction mixture is added to the drying column and allowed to collect in the same vessel as the first extract.

A third extraction of the sample is done with 10 ml of toluene and sonication for 5 minutes in a water bath and the supernatant of this extraction chromatographed through the drying column and added to the first two extraction samples. The collected sample extracts are concentrated by vacuum centrifugation to dryness and resolubilized in hexane.

EXAMPLE 3

Preparation of Liquid Samples for Quantification of TEQs of PCDHs

One to five grams of sample are weighed out into 50 ml centrifuge tubes. One ml of XCARB filtered formic acid is added, the solution is agitated and then allowed to stand for 15 minutes. 30 ml of acetone is added to the sample, the sample is agitated and allowed to settle for 2 minutes. 10 ml of hexane is added to the sample and the sample agitated, then allowed to separate into separate organic and aqueous phases (about 10 minutes).

A drying column is prepared to pass the sample extract through for collection purposes. The drying column consists of a 25 ml glass column to which a glass wool plug has been added to retain packing materials. The first packing material added to the drying column consists is 1 cc of Celite® followed by 4.3 cc of sodium sulfate. The drying column is washed with 30 ml of hexane before collection of sample extracts.

The top phase is transferred to the drying column and allowed to collect in a 50 ml centrifuge tube or other collection vessel. To the sample is added an additional 10 ml of hexane; the shaking and extraction procedure is repeated. The upper phase is removed after allowing separation and passed through the drying column. The extraction procedure is repeated for a third time with an additional 10 ml of hexane and pooled after chromatography through the drying column with the first two extracts.

EXAMPLE 4

Acid-Silica Chromatography

Acid-coated silica gel is prepared by adding concentrated sulfuric acid to activated silica gel in proportions of 1:2 or 33% by weight and allow to stand for 24 hours before use. Acid coated silica gel prepared in this manner is generally useful for 30 days. An acid coated silica gel column is prepared by placing a plug of glass wool in a 10 ml glass drying column, adding one cc of sodium sulfate, and placed over this 4.33 cc of acid coated silica gel, and finally one cc of sodium sulfate. The column is rinsed with 30 ml of hexane which is discarded.

After being resolubilized in hexane, samples extracted by the methods set forth above in Examples 2 and 3 are vortexed vigorously. The solubilized sample is applied to the acid silica column and the tube rinsed twice with 2 ml of hexane, which is also applied to the column. All material eluted from the column is collected in a 50 ml glass centrifuge tube. The column is eluted twice with 10 ml of hexane and pooled with the initial column eluants. The sample is dried to dryness in a vaccuum concentrator and stored for application to the carbon column procedure, below.

EXAMPLE 5

XCARB Column Procedure

Two ml of hexane is added and vigorously vortexed with the sample concentrate from the acid coated silica gel chromatography from Example 4. The sample is applied to a XCARB column prepared as set forth in Example 1. The sample vessel is rinsed with 1 ml of hexane and twice more with 2 ml of hexane and applied to the column. The column is then initially washed with 5 ml of hexane followed by an additional 5 ml of hexane. These washes are discarded. A collection tube (16 mm glass tube) is placed under the column to collect the fraction containing PCBs. PCBs are eluted by eluting the column with 15 ml of a solution containing 10% toluene/10% ethyl acetate/80% hexane. The PCB fraction is concentrated to dryness and prepared for CALUX® analysis. Another collection tube (50 ml glass tube) is placed under the column to collect the dioxin/furan material. The dioxin/furan fraction is eluted with 20 ml of toluene. The sample is concentrated to dryness and prepared for CALUX® analysis and induction of luciferase activity.

EXAMPLE 6

Preparation of Sample Concentrates for CALUX® Analysis

CALUX® analysis is generally carried out as follows: As set forth above, cell line mouse hepatoma H1L.1 is stably transfected with a vector that contains the gene for firefly luciferase under transactivational control of the aryl hydrocarbon receptor. See P. M. Garrison, et al., Fundam. Appl. Toxicol. 30, 194–203 (1996); U.S. Pat. No. 5,854,010 to Denison et al., incorporated by reference herein. Serial dilutions of the compounds of interest are prepared in dimethyl sulfoxide (DMSO). Prior to dosing the cells, the DMSO solutions are suspended in cell culture medium and the medium added to monolayers of the cells grown in 96-well culture plates. In addition to the samples, a standard curve of TCDD is assayed (a two-fold dilution series beginning at $1.55 \times 10^{-9}$ M TCDD). The plates are generally incubated for about 20 hours at 37° C. in a humidified $CO_2$ incubator to allow optimal luciferase gene expression. Following incubation, the medium is removed and the cells examined microscopically for viability. The induction of luciferase activity is quantified using the luciferase assay kit from Promega (Madison, Wis.).

With regard to data analysis, the response for each concentration of each compound that reached a maximal response is generally analyzed at least three times. Data for the dose response series are fit to a sigmoid curve described by the Hill Equation using least squares, best fit modeling. The values for the maximal response and concentrations associated with 20–80% of the maximal response ($EC_{20-80}$) are determined from the derived Hill Equation for each compound. The maximal response for each of the compounds is compared to the maximal response for the standard TCDD using a two-tailed student's t-test with $\alpha=0.05$.

Using the foregoing general protocol, sample concentrates or dilutions of sample concentrates produced as in Example 5 are solubilized in one ml of hexane, and four ml of DMSO is added to the tube. The sample is concentrated to dryness using vacuum centrifugation. To the tube is added 0.4 ml of cell culture medium containing RPMI 1640, 8% Fetal Bovine Serum. The sample is vortexed vigorously and applied to monolayers of our patented recombinant cells. The cells are incubated with a standard curve dilution of 2,3,7,8-tetrachlordibenzo-p-dioxin and samples and incubated to induce maximal concentrations of the luciferase from the stable transfected reporter gene construct. Following incubation cells are lysed and luciferase activity measured. The TEQ activity contained in processed samples is quantified by comparison to the luciferase activity induced by the standard 2,3,7,8-tetrachlordibenzo-p-dioxin.

EXAMPLE 7

Analysis of Results

Figure 3:
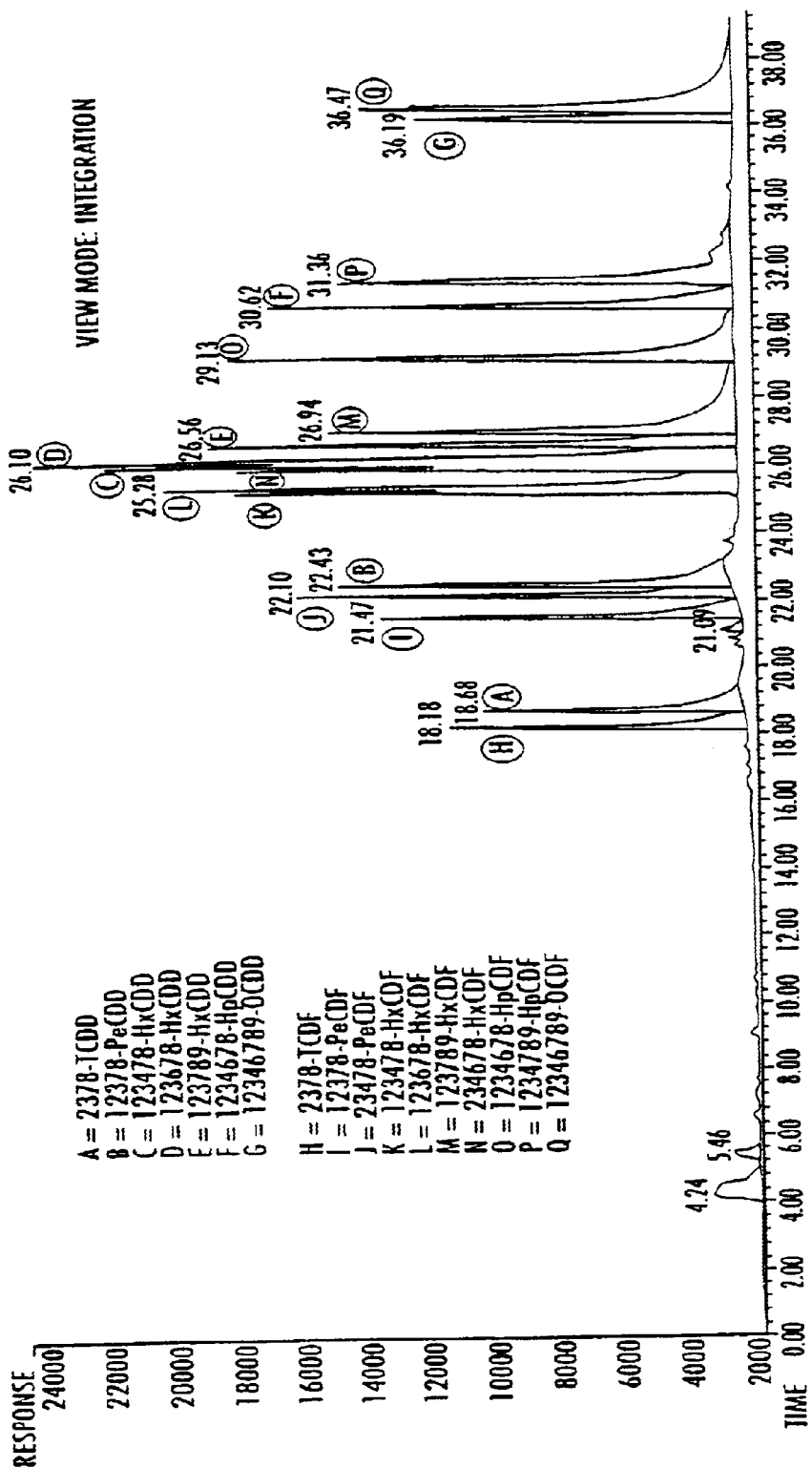
FIG. 3 is a chromatograph of polychlorinated dibenzodioxins that were used to make the total mixture in FIG. 2 prior to processing by the methods of the present invention, as measured by gas chromatography and electron capture detection.
Figure 4:
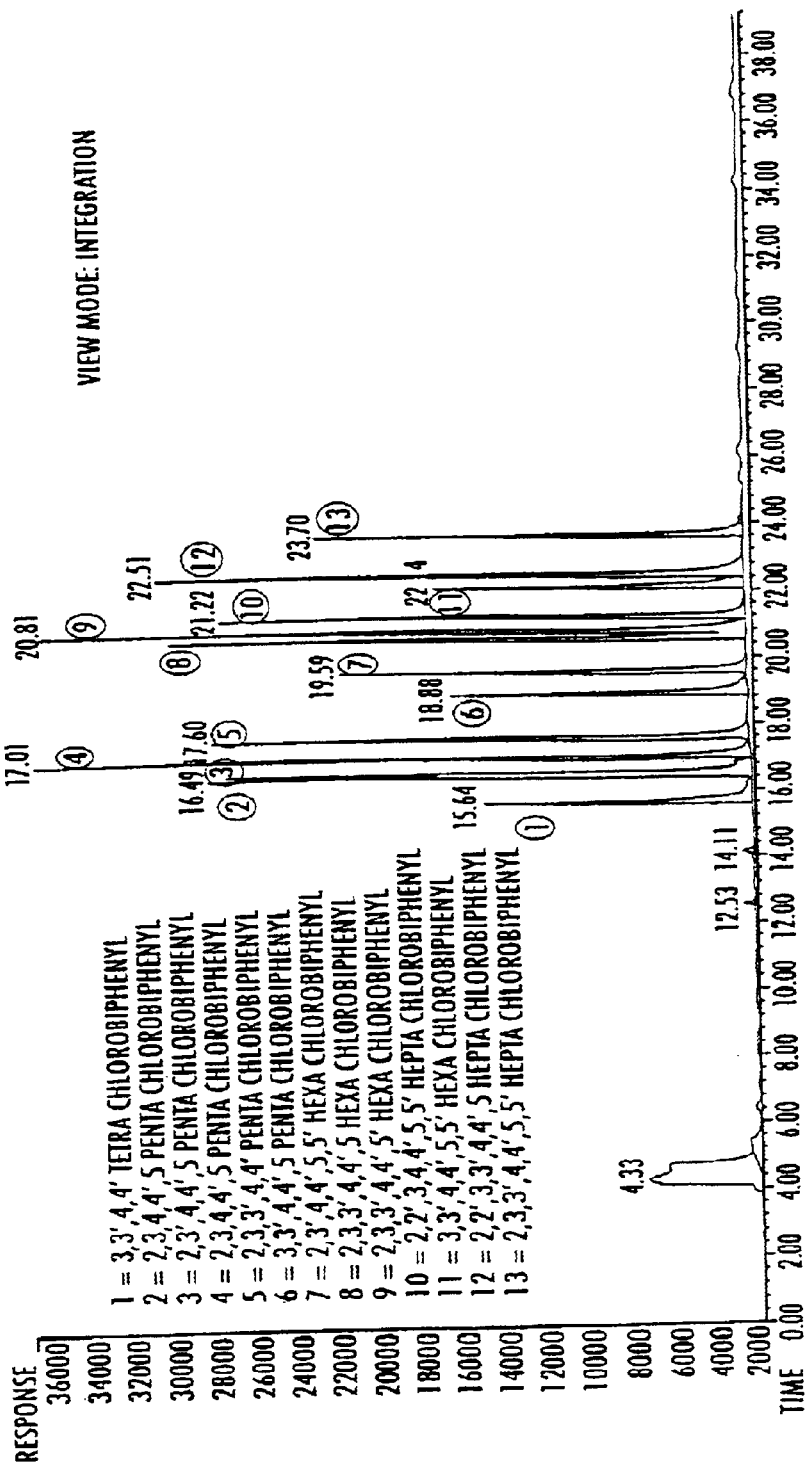
FIG. 4 is a chromatograph of polychlorinated biphenyls that were used to make the total mixture in FIG. 2 prior to processing by the methods of the present invention, as measured by gas chromatography and electron capture detection.

FIG. 2 displays the chromatogram profile of a representative mixture of PCBs and dioxins and furans obtained by gas chromatography and electron capture detection. This total mixture contains the majority of PCDHs that have been assigned Toxic Equivalency Factors (TEF) by the World Health Organization (WHO). In comparison, FIG. 3 displays the chromatogram profile using gas chromatography and electron capture detection of the dioxins and furans in the mixture. The peaks missing from FIG. 3 represent the contribution of PCBs to the mixture. In contrast, FIG. 4 displays the chromatogram profile using gas chromatography and electron capture detection of the PCBs in the mixture and the peaks that are characteristic of the dioxins and furans are absent from this chromatogram.

To illustrate the efficacy of the present invention, the representative mixture of PCDHs was chromatographed on the XCARB matrix of the present invention, according to the Examples set forth above.

Figure 5:
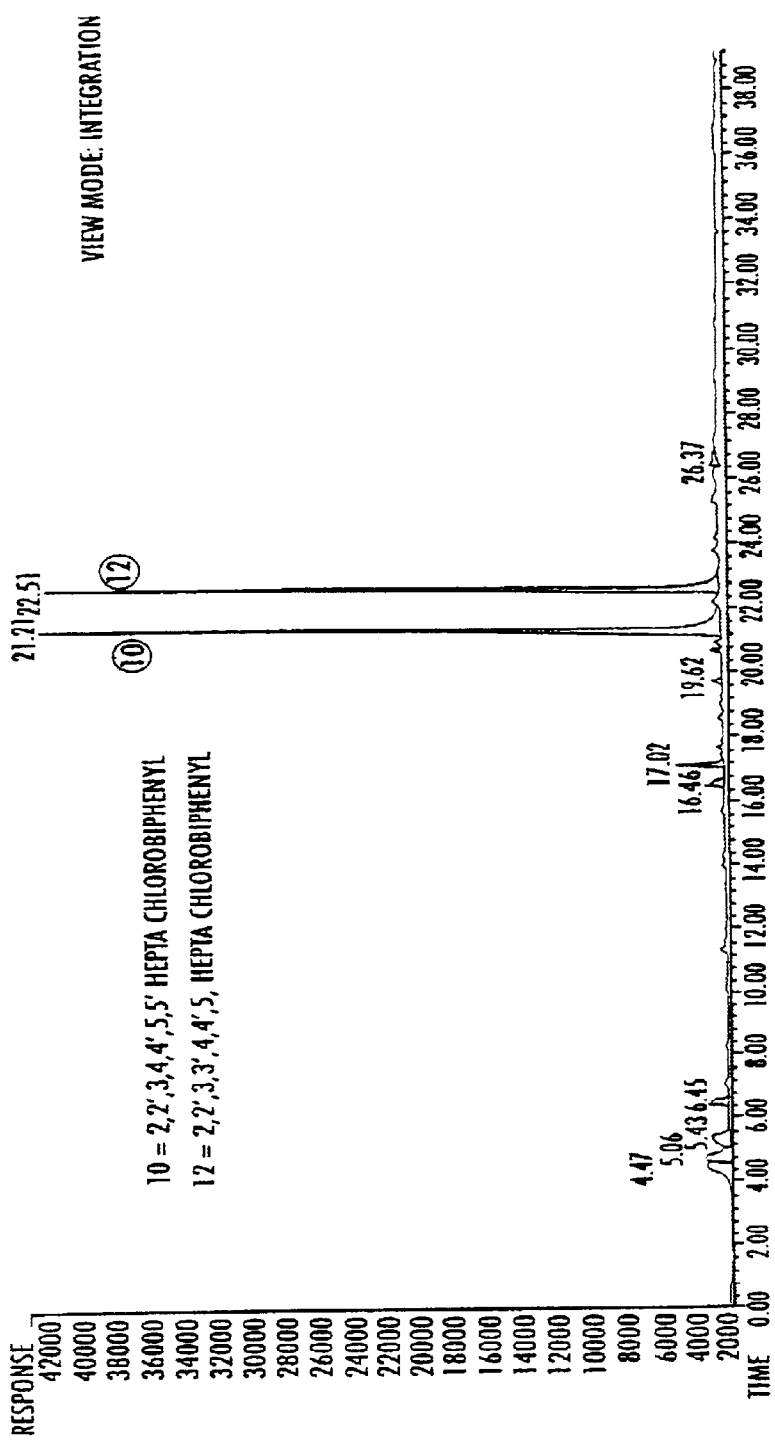
FIG. 5 is a chromatograph of polychlorinated biphenyls that were not retained on an XCARB column adsorption matrix of the present invention, as measured by gas chromatography and electron capture detection.
Figure 7:
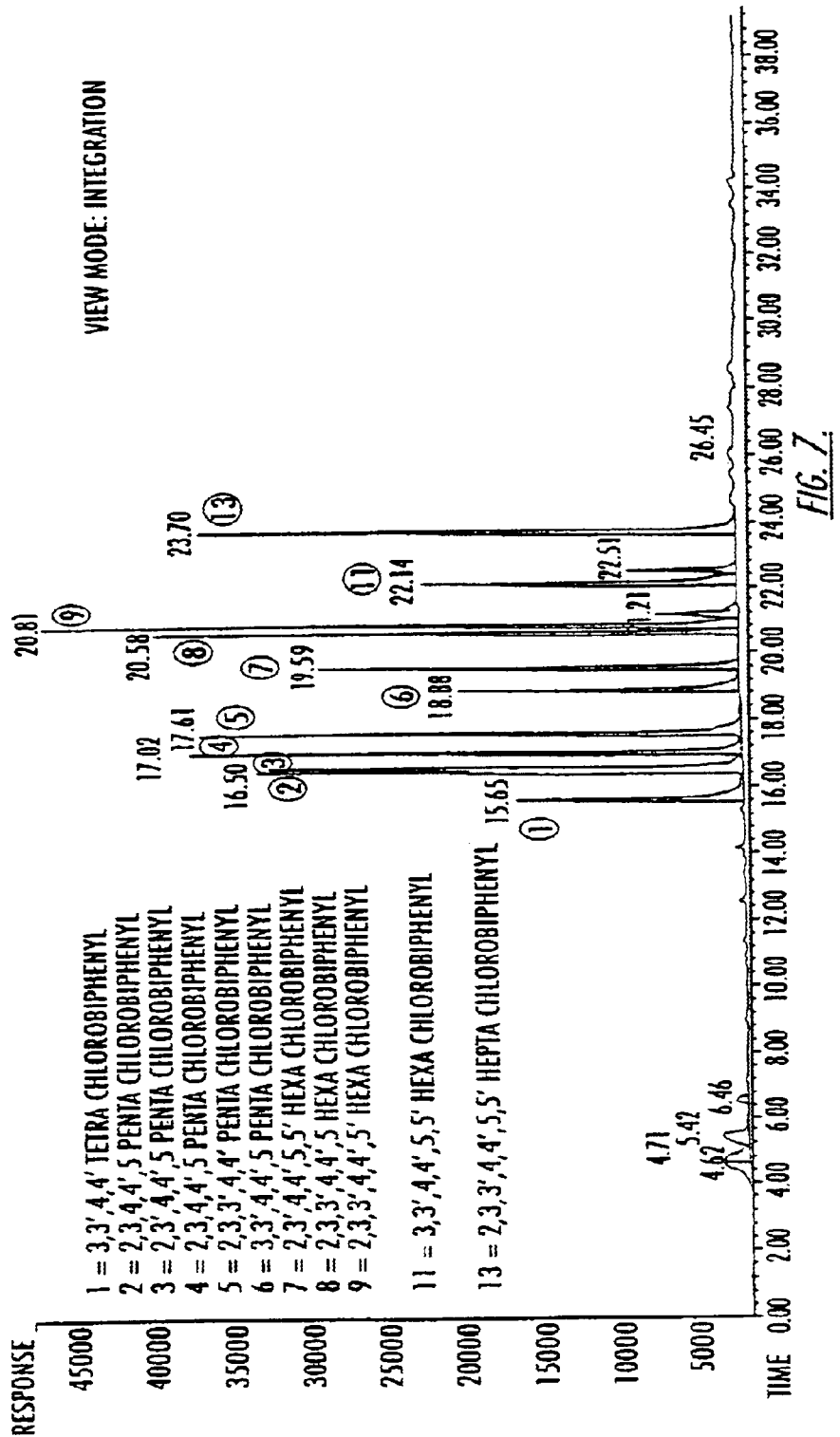
FIG. 7 is a chromatograph of the mixture of polychlorinated biphenyls that were selectively retained on the XCARB column adsorption matrix of the present invention and subsequently selectively eluted for PCBs, as measured by gas chromatography and electron capture detection.

FIG. 5 is a chromatogram of those isomers that were not retained on the absorbent. These peaks on the chromatogram are indicative of PCBs 170 and 180, which do not possess TEF values. FIG. 7 is a chromatogram of the selective elution of PCBs from the XCARB affinity column and matches very closely with FIG. 4 (the chromatogram of the PCBs). However, the peaks for PCB 170 and 180 which were not retained by the XCARB matrix are missing.

Figure 6:
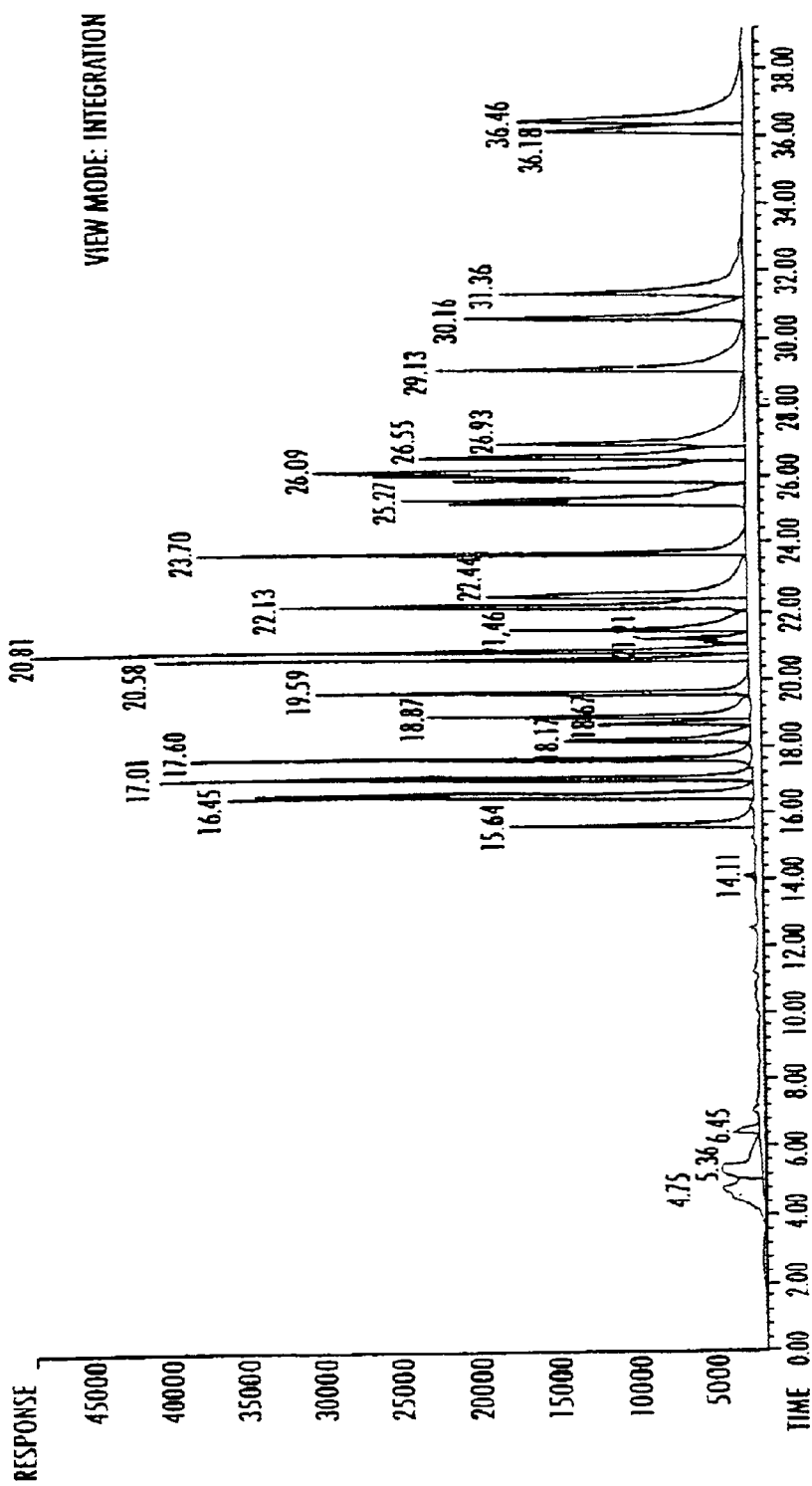
FIG. 6 is a chromatograph of polychlorinated biphenyls and polychlorinated dibenzodioxins/furans that were retained and eluted on the XCARB column adsorption matrix of the present invention to isolate total PCDHs, as measured by gas chromatography and electron capture detection.

FIG. 6 is the chromatogram of the PCDHs including PCBs, dioxins and furans eluted from the XCARB matrix. These data demonstrate that the XCARB matrix is capable of retaining PCDHs, while the present inventive methods are able to quantitatively recover these PCDH isomers from the matrix. This material and process can be linked with the recombinant bioassay procedure set forth in the '010 patent (the CALUX® system) to provide a sensitive analytical system for the detection of PCDHs in environmental matrices.

Figure 8:
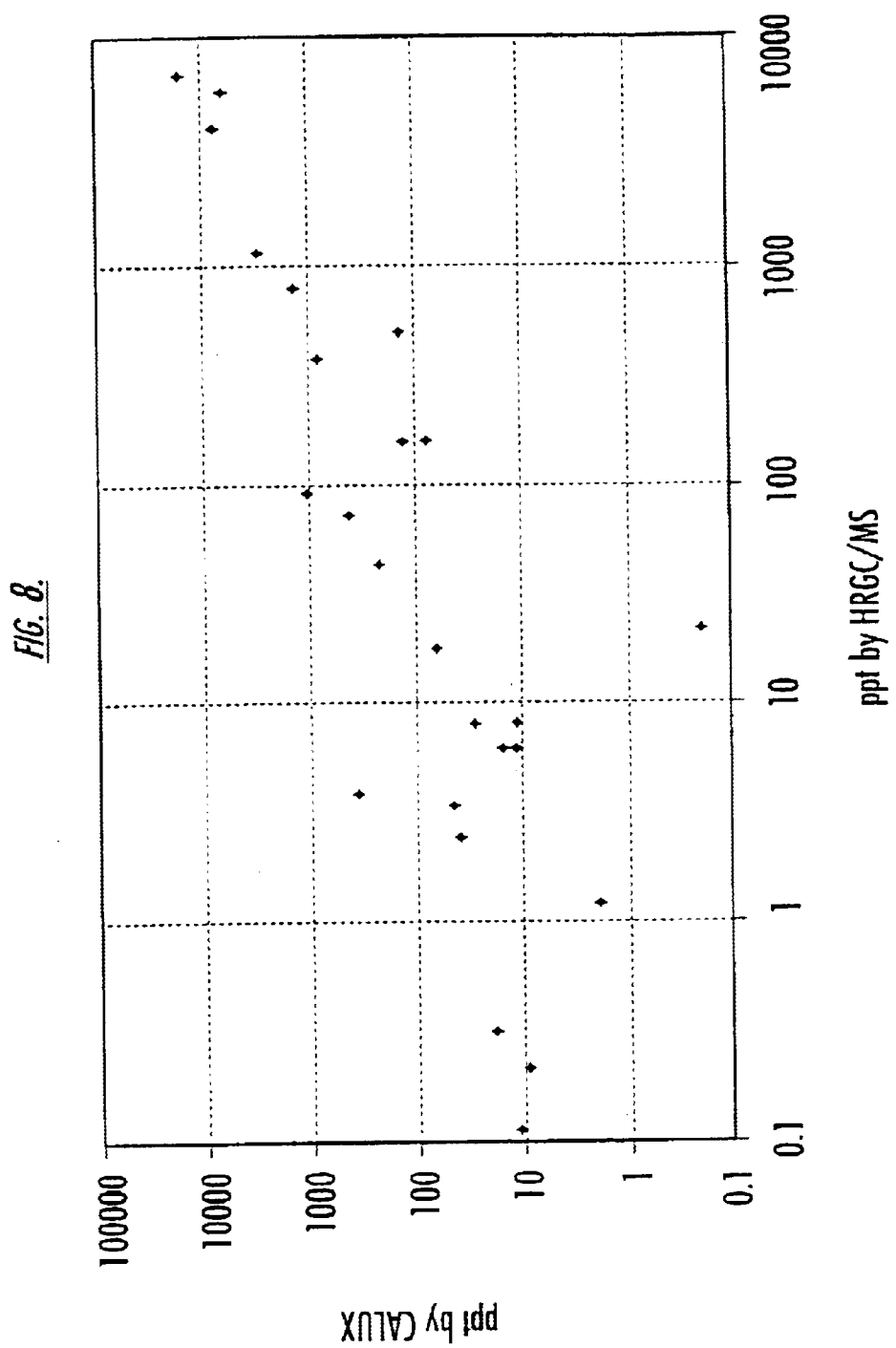
FIG. 8 is a graphical representation of correlation data comparing CALUX® TEQ determinations with HRGC/HRMS determinations of TEQ activity for soil and ash samples.

FIG. 8 illustrates the correlation of TEQ activity of soil and ash samples quantified using the CALUX® bioassay with the processing system of the present invention versus quantification using high resolution gas chromatography/ high resolution mass spectrometry. The results correspond highly, with a correlation coefficient of 0.94.

Figure 9:
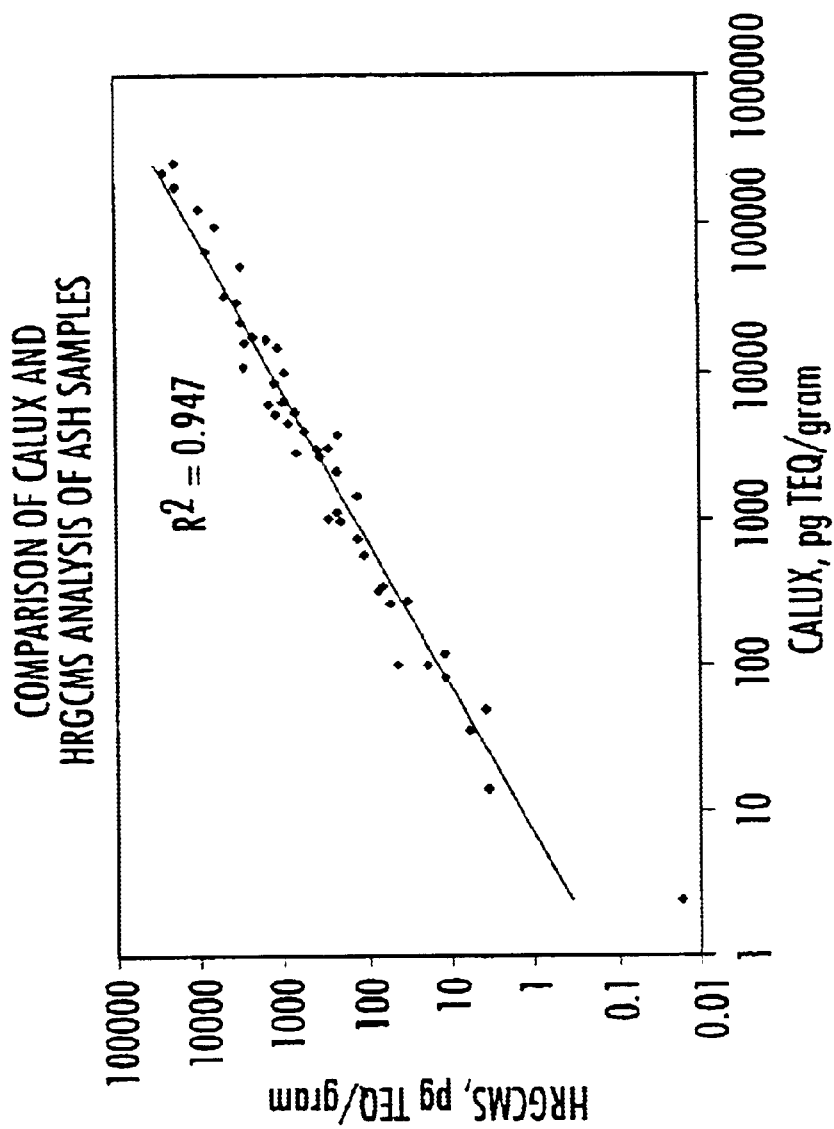
FIG. 9 is a graphical representation of correlation data comparing CALUX® TEQ determinations with HRGC/HRMS determinations of TEQ activity for ash samples.

FIG. 9 illustrates the correlation of TEQ activity of ash samples quantified using the CALUX® bioassay with the processing system of the present invention versus quantification using high resolution gas chromatography/high resolution mass spectrometry.

Figure 10:
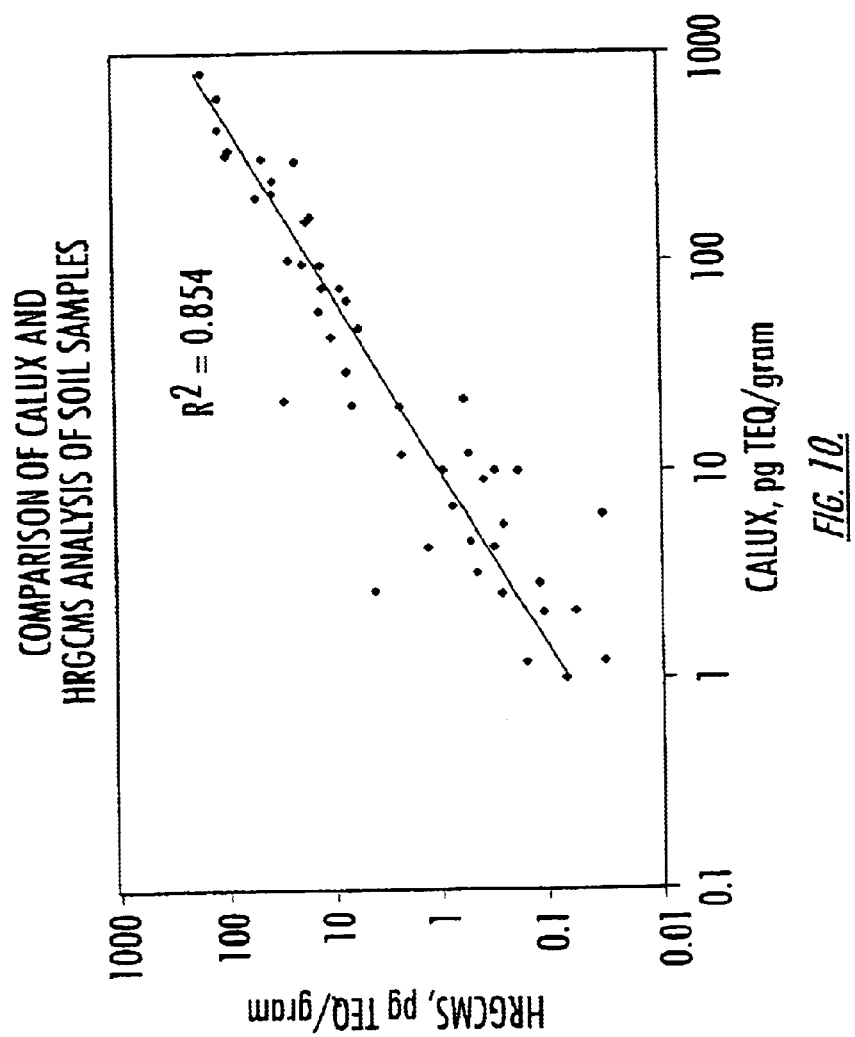
FIG. 10 is a graphical representation of correlation data comparing CALUX® TEQ determinations with HRGC/HRMS determinations of TEQ activity for soil samples.

FIG. 10 illustrates the correlation of TEQ activity of ash samples quantified using the CALUX® bioassay with the processing system of the present invention versus quantification using high resolution gas chromatography/high resolution mass spectrometry.

Figure 11:
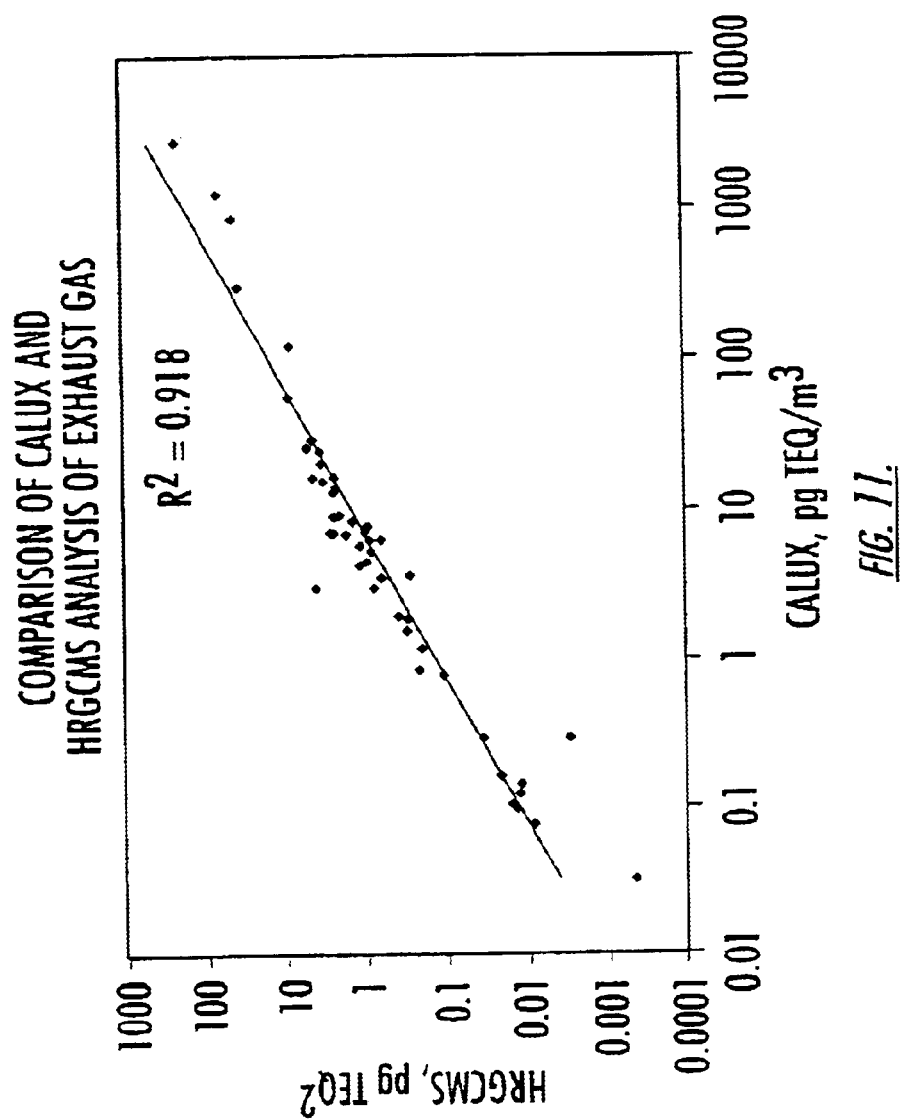
FIG. 11 is a graphical representation of correlation data comparing CALUX® TEQ determinations with HRGC/HRMS determinations of TEQ activity for exhaust gas samples.

FIG. 11 illustrates the correlation of TEQ activity of exhaust gas samples quantified using the CALUX® bioassay with the processing system of the present invention versus quantification using high resolution gas chromatography/high resolution mass spectrometry. These data demonstrate the usefulness of combining the CALUX® bioassay with the present inventive methods for providing data on TEQ contamination of samples for risk assessment purposes to protect the environment and human health.

The foregoing is illustrative of the present invention and is not to be construed as limiting thereof. The invention is defined by the following claims, with equivalents of the claims to be included therein.

That which is claimed is:

1. A method of separating polyhalogenated biphenyl compounds (PHBs), polyhalogenated dibenzofurans (PHDFs) and polyhalogenated dibenzo-p-dioxins (PHDDs) from a mixture of polyhalogenated diaromatic hydrocarbons, comprising:
   extracting a sample with an organic solvent to produce a first extracted sample comprising polyhalogenated diaromatic hydrocarbons;
   contacting said first extracted sample with an adsorption matrix comprising activated carbon and diatomaceous earth, wherein said activated carbon has been heated prior to contact with the first extracted sample, and wherein PHB, PHDD and PHDF compounds adsorb onto the matrix;
   eluting the PHB compounds from the matrix to produce a PHB fraction; and
   eluting the PHDD and PHDF compounds from the matrix to produce a PHDD/PHDF fraction.

2. The method of claim 1, wherein the mixture of polyhalogenated diaromatic hydrocarbons comprises polychlorinated diaromatic hydrocarbons.

3. The method of claim 1, wherein the mixture of polyhalogenated diaromatic hydrocarbons comprises polybrominated diaromatic hydrocarbons.

4. The method of claim 1, wherein the mixture of polyhalogenated diaromatic hydrocarbons comprises mixed brominated/chlorinated diaromatic hydrocarbons.

5. The method of claim 1, wherein the PHB fraction comprises polybrominated biphenyl compounds (PBBs).

6. The method of claim 1, wherein the PHB fraction comprises polychlorinated biphenyl compounds (PCBs).

7. The method of claim 1, wherein the PHDD/PHDF fraction comprises polybrominated dibenzofurans (PBDFs).

8. The method of claim 1, wherein the PHDD/PHDF fraction comprises polychlorinated dibenzo-p-dioxins (PCDFs).

9. The method of claim 1, wherein the PHDD/PHDF fraction comprises polybrominated dibenzofurans (PBDFs).

10. The method of claim 1, wherein the PHDD/PHDF fraction comprises polychlorinated dibenzo-p-dioxins (PCDFs).

11. The method of claim 1, wherein the first extracted sample is purified by separating the sample on a matrix comprising sodium sulfate.

12. The method of claim 1, wherein the first extracted sample is further purified by separating the first extracted sample on a column comprising silica gel.

13. The method of claim 12, wherein the column comprising silica gel is treated with sulfuric acid prior to purifying the first extracted sample.

14. The method of claim 1, wherein the activated carbon is graphitized carbon.

15. The method of claim 1, wherein the PHDD/PHDF fraction comprises one or more of a compound selected from the group consisting of 2,3,7,8-tetrachlorodibenzodioxin, 2,3,7,8-tetrachlorodibenzofuran, and their isomers.

16. The method of claim 1, wherein the sample is a liquid sample.

17. The method of claim 1 wherein the sample is a solid sample.

18. The method of claim 1 wherein the sample is a gaseous sample.

19. The method of claim 1, wherein the sample is selected from the group consisting of soil samples and ash samples.

20. The method of claim 1, further comprising determining the toxicity of the PHB fraction.

21. The method of claim 20, wherein the toxicity is determined by a cell-based assay.

22. The method of claim 21, wherein the cell based assay comprises measuring the expression of luciferase in cell line ATCC CRL-12286 in response to the concentration of PHB in the PHB fraction.

23. The method of claim 1, further comprising determining the toxicity of the PHDD/PHDF fraction.

24. The method of claim 23, wherein the toxicity is determined by a cell-based assay.

25. The method of claim 24, wherein the cell based assay comprises measuring the expression of luciferase in cell line ATCC CRL-12286 in response to the concentration of PHDD/PHDF compounds in the PHDD/PHDF fraction.

26. A method of separating polychlorinated biphenyl compounds (PCBs), polychlorinated dibenzofurans (PCDFs), and polychlorinated dibenzo-p-dioxins (PCDDs) from a mixture of polychlorinated diaromatic hydrocarbons, comprising:
   extracting a sample with an organic solvent to produce a first extracted sample comprising polychlorinated diaromatic hydrocarbons;
   contacting said first extracted sample with an adsorption matrix comprising activated carbon and diatomaceous earth, wherein said activated carbon has been heated prior to contact with the first extracted sample, and wherein PCB, PCDD and PCDF compounds adsorb onto the matrix;
   eluting the PCB compounds from the matrix to produce a PCB fraction; and
   eluting the PCDD and PCDF compounds from the matrix to produce a PCDD/PCDF fraction.

27. The method of claim 26, wherein the first extracted sample is purified by separating the sample on a matrix comprising sodium sulfate.

28. The method of claim 26, wherein the first extracted sample is further purified by separating the first extracted sample on a column comprising silica gel.

29. The method of claim 28, wherein the column comprising silica gel is treated with sulfuric acid prior to purifying the first extracted sample.

30. The method of claim 26, wherein the activated carbon is graphitized carbon.

31. The method of claim 26, wherein the PCDD/PCDF fraction comprises one or more of a compound selected from the group consisting of 2,3,7,8-tetrachlorodibenzodioxin, 2,3,7,8-tetrachlorodibenzofuran, and their isomers.

32. The method of claim 26, wherein the sample is a liquid sample.

33. The method of claim 26, wherein the sample is a solid sample.

34. The method of claim 26 wherein the sample is a gaseous sample.

35. The method of claim 26, wherein the sample is selected from the group consisting of soil samples and ash samples.

36. The method of claim 26, further comprising determining the toxicity of the PCB fraction.

37. The method of claim 36, wherein the toxicity is determined by a cell-based assay.

38. The method of claim 37, wherein the cell based assay comprises measuring the expression of luciferase in cell line ATCC CRL-12286 in response to the concentration of PCB in the PCB fraction.

39. The method of claim 26, further comprising determining the toxicity of the PCDD/PCDF fraction.

40. The method of claim 39, wherein the toxicity is determined by a cell-based assay.

41. The method of claim 40, wherein the cell based assay comprises measuring the expression of luciferase in cell line ATCC CRL-12286 in response to the concentration of PCDD/PCDF compounds in the PCDD/PCDF fraction.

42. A method of comparing the amount of PCBs relative to the amount of PCDDs and PCDFs in a sample comprising a mixture of polychlorinated diaromatic hydrocarbons, comprising:

extracting a sample with an organic solvent to produce a first extracted sample comprising polychlorinated diaromatic hydrocarbons;

contacting said first extracted sample with an adsorption matrix comprising activated carbon and diatomaceous earth, wherein said activated carbon has been heated prior to contact with the first extracted sample, and wherein PCB, PCDD and PCDF compounds adsorb onto the matrix;

eluting the PCB compounds from the matrix to produce a PCB fraction;

determining the amount of PCBs present in the PCB fraction;

eluting the PCDD and PCDF compounds from the matrix to produce a PCDD/PCDF fraction;

determining the amount of PCDDs and PCDFs present in the PCDD/PCDF fraction; and then comparing the amount of PCBs in the PCB fraction with the amount of PCDDs and PCDFs present in the PCDD/PCDF fraction.

43. The method of claim 42, wherein the extracting of the sample is carried out by separating the sample on a matrix comprising sodium sulfate.

44. The method of claim 42, further comprising purifying the first extracted sample by separating the sample on a column comprising silica gel.

45. The method of claim 42, wherein the column is treated with sulfuric acid.

46. The method of claim 42, wherein the activated carbon is graphitized carbon.

47. The method of claim 42, wherein the sample is a liquid sample.

48. The method of claim 42, wherein the sample is a solid sample.

49. The method of claim 42, wherein the sample is a gaseous sample.

50. The method of claim 42, wherein the sample is selected from the group consisting of soil samples and ash samples.

51. The method of claim 42, wherein the PCDD/PCDF fraction comprises one or more of a compound selected from the group consisting of 2,3,7,8-tetrachlorodibenzodioxin, 2,3,7,8-tetrachlorodibenzofuran, and their isomers.

52. The method of claim 42, wherein the amount of PCBs present in the PCB fraction is determined by high resolution gas chromatography mass spectroscopy.

53. The method of claim 42, wherein the amount of PCDD and PCDF compounds present in the PCDD/PCDF fraction is determined by high resolution gas chromatography mass spectroscopy.

54. A method of separating polychlorinated biphenyl compounds (PCBs), polychlorinated dibenzofurans (PCDFs), and polychlorinated dibenzo-p-dioxins (PCDDs) from a mixture of polychlorinated diaromatic hydrocarbons, comprising:

extracting a sample with an organic solvent to produce a first extracted sample comprising polychlorinated diaromatic hydrocarbons;

purifying the first extracted sample by separating the first extracted sample on a purification matrix comprising sodium sulfate;

further purifying the first extracted sample by separating the first extracted sample on a column comprising silica gel to produce a purified first extracted sample, wherein the column comprising silica gel is treated with sulfuric acid prior to purifying the first extracted sample;

contacting said first extracted sample with an adsorption matrix comprising activated carbon and diatomaceous earth, wherein said activated carbon has been heated prior to contact with the first extracted sample, and wherein PCB, PCDD and PCDF compounds adsorb onto the matrix;

eluting the PCB compounds from the adsorption matrix to produce a PCB fraction; and eluting the PCDD and PCDF compounds from the adsorption matrix to produce a PCDD/PCDF fraction.

55. The method of claim 54, wherein the activated carbon is AX-21.

56. The method of claim 55, wherein the AX-21 is heated prior to contacting the first extracted sample.

57. The method of claim 54, wherein the activated carbon is GRAFOIL® grade TG-407 flexible graphite powder.

58. The process of claim 1, wherein the activated carbon is an activated carbon molecular sieve.

59. The process of claim 1, wherein said activated carbon was heated to a temperature of at least about 100° C.

60. The process of claim 1, wherein said activated carbon was heated to a temperature of about 200° C. to about 250° C.

61. The process of claim 1, wherein said activated carbon was heated for a time of at least about one hour.

62. The process of claim 1, wherein said activated carbon was heated for a time of at least about one day.

63. The process of claim 1, wherein said activated carbon was heated for a time of at least about one week.

64. The process of claim 1, wherein said activated carbon was heated for a time of at least about thirty days.

65. The process of claim 26, wherein the activated carbon is an activated carbon molecular sieve.

66. The process of claim 26, wherein said activated carbon was heated to a temperature of at least about 100° C.

67. The process of claim 26, wherein said activated carbon was heated to a temperature of about 200° C. to about 250° C.

68. The process of claim 26, wherein said activated carbon was heated for a time of at least about one hour.

69. The process of claim 26, wherein said activated carbon was heated for a time of at least about one day.

70. The process of claim 26, wherein said activated carbon was heated for a time of at least about one week.

71. The process of claim 26, wherein said activated carbon was heated for a time of at least about thirty days.

72. The process of claim 42, wherein the activated carbon is an activated carbon molecular sieve.

73. The process of claim 42, wherein said activated carbon was heated to a temperature of at least about 100° C.

74. The process of claim 42, wherein said activated carbon was heated to a temperature of about 200° C. to about 250° C.

75. The process of claim 42, wherein said activated carbon was heated for a time of at least about one hour.

76. The process of claim 42, wherein said activated carbon was heated for a time of at least about one day.

77. The process of claim 42, wherein said activated carbon was heated for a time of at least about one week.

78. The process of claim 42, wherein said activated carbon was heated for a time of at least about thirty days.

79. The process of claim 54, wherein the activated carbon is an activated carbon molecular sieve.

80. The process of claim 54, wherein said activated carbon was heated to a temperature of at least about 100° C.

81. The process of claim 54, wherein said activated carbon was heated to a temperature of about 200° C. to about 250° C.

82. The process of claim 54, wherein said activated carbon was heated for a time of at least about one hour.

83. The process of claim 54, wherein said activated carbon was heated for a time of at least about one day.

84. The process of claim 54, wherein said activated carbon was heated for a time of at least about one week.

85. The process of claim 54, wherein said activated carbon was heated for at least thirty days.

\* \* \* \* \*